United States Patent [19]

Benckhuijsen

[11] Patent Number: 5,439,480

[45] Date of Patent: Aug. 8, 1995

[54] METHOD OF USING A WOVEN CLOTH TO INCREASE OXYGEN PARTIAL PRESSURE IN MUSCULATURE

[75] Inventor: Gerrit J. Benckhuijsen, Eschen, Liechtenstein

[73] Assignee: Temova Etablissement, Schaan, Liechtenstein

[21] Appl. No.: 137,119

[22] PCT Filed: Apr. 24, 1992

[86] PCT No.: PCT/EP92/00909

§ 371 Date: Oct. 25, 1993

§ 102(e) Date: Oct. 25, 1993

[87] PCT Pub. No.: WO92/19180

PCT Pub. Date: Nov. 12, 1992

[30] Foreign Application Priority Data

Apr. 25, 1991 [CH] Switzerland .................. 1241/91

[51] Int. Cl.⁶ ........................................... A61B 17/00
[52] U.S. Cl. ............................................. 607/1
[58] Field of Search ................ 607/1; 601/15; 602/60

[56] References Cited

U.S. PATENT DOCUMENTS 4,834,079  5/1989  Benckhuijsen .................. 128/82.1

FOREIGN PATENT DOCUMENTS 0059917  1/1982  European Pat. Off. .
1231117  4/1959  France .
 336038  9/1955  Germany .
1572250 12/1976  United Kingdom .

OTHER PUBLICATIONS

Frank-Dietmar Ernst, "Funktionelle Beziehungen zwischen Mikrozirkulation und Sauerstoffversorgung", *Zeitschrift Fur Die Gesamte Innere Medizin Und Ihre Grenzgebiete*, vol. 40, Issue 9, 1 May 1985.

*Primary Examiner*—William E. Kamm
*Attorney, Agent, or Firm*—Oliff & Berridge

[57] ABSTRACT

A woven cloth comprised of at least 50% by weight of polyvinyl chloride and/or polyamide fibers and, if necessary, acrylic fibers, but, in any case, less than 10% by weight of cotton and/or rayon fibers, is used as a therapeutic aid to increase the oxygen partial pressure in animal or human musculature. The woven cloth preferably is comprised of at least 50% by weight of polyvinyl chloride fibers, preferably more than 75% by weight of polyvinyl chloride fibers, and a maximum of 25% by weight of acrylic and/or polyester fibers. The woven cloth is used to produce bandages or stockings, for example.

16 Claims, 12 Drawing Sheets

METHOD OF USING A WOVEN CLOTH TO INCREASE OXYGEN PARTIAL PRESSURE IN MUSCULATURE

BACKGROUND

A reduced oxygen level in human or animal tissue can be regarded as the primary cause of many complaints. A branch of medical research therefore has for its object to find or improve methods which render an increased supply of oxygen to the tissue possible.

For several medical indications methods can be used which are to render an increased supply of oxygen/-possible. Known methods are, for example, the oxygenation, the oxygen multi-step therapy or also the hyperbaric medicine or the external application of activated, molecular oxygen, as present in tetrachlorodecaoxide. Each of these methods has for certain indications its advocates and produces results but it should not be ignored that just in this field the opinions differ widely. One of the reasons being no doubt the fact that an improved oxygen absorption also involves certain risks which arise from the formation to some extent of dangerous oxygen species such as Singulett oxygen, hydroxyl radicals, superoxide radicals and peroxide. Moreover, many applications per se are not without danger, examples thereof being the hyperbaric medicine or injections of a person's own oxygen-enriched blood.

SUMMARY OF THE INVENTION

Therefore the present invention has for its object, to provide a harmless method which renders an increased absorption of oxygen by human or animal tissue possible. This is accomplished by the use of a woven cloth composed of at least 50% by weight of polyvinyl chloride and/or polyamide fibers, which if necessary also contains acrylic fibers, in any case however less than 10% cotton and/or rayon fibers for producing a therapeutic aid for increasing the oxygen partial pressure in animal or human musculature.

"(Woven) cloth" must here be understood to mean any type of flat textile fabrics in which the thread combination of the different fibers can be effected in the form of weaves, weft-knitted fabrics, warp-knitted fabrics, tissues or also fleecy fabrics.

It is known that woven cloths made of certain artificial fibers, more particularly a mixture of polyvinyl chloride and acrylic fibers have particularly advantageous physico-chemical properties. They are, for example, characterized, because of the poor thermal conductivity of the fibers, by a high insulating power. In addition, the fibers are water-repellent and do not swell, so that moisture on the skin is immediately transferred to the exterior by the cloth. Added to this is the fact that when these synthetic fibers are worn, frictional electricity is produced; this has a stimulating effect on the skin and the skin appendages, which is considered an extremely pleasant property of such a fiber fabric.

These advantageous, known properties of the cloth are utilized in, for example, the treatment of pain syndromes and its use as a woven cloth for orthopaedic, therapeutic foundation garments and bandages is recommended and they proved to be effective either as cervical collars, shoulder joint bandages or lumbar ortheses, or as bandages for the extremities. In the same manner these cloths have proved their worth in veterinary medicine for bandages of the sensitive tendons and joints of horses, which are prone to swelling.

A hyperemia of the skin during wearing of these cloths has indeed occurred, but this fact does in no way suggest, as can, for example, be read from the Zeitschrift für die gesamte Innere Medizin, published Jan. 5, 1995 (Leipzig), that this is accompanied by an increase in the oxygen partial pressure in the musculature. This surprising effect was not detected until after a large number of measurements of the oxygen partial pressure in the musculature in the leg and the back.

The results of these tests performed on sportsmen and non-sportsmen, older and younger ones, healthy and sick persons, recommend the use of such a cloth, for example Vibrostatic ® (registered trademark of Messra, Temova Establishment, Vaduz), to produce therapeutic aids, such as bandages, underwear, gloves or stockings, as a supporting treatment for acute and chronic low oxygen level syndromes due to a disturbed microcirculation. Examples of indications are therefore tendinose, condylopathy, torticollis, restless legs, Sudeck syndrome, Raynaud disease, Buerger disease, diabetic angiopathy, a tendency towards muscle cramp, more specifically of the calf musculature, and arterial occlusion diseases. Clothing for sportsmen made from these woven cloths can be recommended in particular as auxilary aids during the warming-up stage, for a faster and more effective loosening of the muscle system. These cloths are also suitable for the production of bandages or stockings as an aid in the treatment of a disturbed blood circulation in the arteries in the limbs, possibly because the oxygen partial pressure which is increased by the woven cloths in accordance with the invention improves the oxygen transition in the muscle tissue. Hence a corresponding utilization in the vetinerary medicine is obvious, more in particular for sport horses but also for dogs, when there are indications of spasmi musculorum, hernia cervicalis, myalgia dorsi, tendinose, tendovaginitis, tendinitis, tumor traumatica, sonantia mala vulneri, podotrochleosis, sesamoidosis, arthrosis, acute and chronic arthritis, and periostitis.

An increase in the oxygen partial pressure in the musculature means an increase in the micro-circulation. This increase in the micro-circulation in deeper tissue layers is from the medical viewpoint not a definite result of the hyperemiasation of the skin or the subcutaneous regions.

The positive, unexpected effects in deeper human or animal tissues when the woven cloths which are suitable for use in accordance with the invention are worn will be evident from the test results, in which the tests comprise a plurality of test series. Their results will be described with reference to the drawing.

DETAILED DESCRIPTION OF PREFERRED EMBODIMENTS

Two test series were performed. In the first test series the oxygen partial pressure in the leg musculature was measured, and in the second test series the oxygen partial pressure in the musculature in the lumbar vertebrae was measured. In accordance with a random test schedule the test persons were clothed with articles such as stockings or bodice-like vests. These foundation garments, which are worn directly on the skin, were made of different fibers. Thus, articles of clothing made of artificial fibers as well as of natural fibres were used, as were mixtures thereof.

These test series show that extreme measuring results can be assigned to two fibers or fiber mixtures.

These two materials are on the one hand pure cotton (negative!) and on the other hand a woven cloth of a mixture of approximately 85% polyvinyl chloride (PVC) and 15% acrylic fibers, hereinafter denoted PVC-A-fiber for the sake of simplicity (positive!). The results for articles of clothing of other fibers or fiber mixtures, respectively, were between the negative extreme values for articles of clothing made of pure cotton and the positive extreme values for articles made of PVC-A-fibers. Particularly good results were obtained for pure PVC-fibers, to a less extent also for pure polyamide fibers and mixtures of these two fiber types. The values for silk and wool or intermixtures of these fibers show a largely natural behaviour, so that adding these fibers to the mixtures in accordance with the invention to obtain given combinations of properties may be useful. The values for angora, which are not included in the survey, can indeed basically also be considered to be positive. That angora wool alone is nevertheless not so suitable for the production of a therapeutic aid is due to the property, which here must be considered as being a negative property, that it absorps moisture. Therefore, when worn directly on the skin, it does not provide a comparable comfortable feeling during wearing as, for example, a clothing article of PVC-A-fiber. Mixtures containing angora and/or PVC-A-fibers can indeed be advantageous for some applications. Also admixtures of silk prove to be advantageous in terms of wearing comfort.

Figure 1:
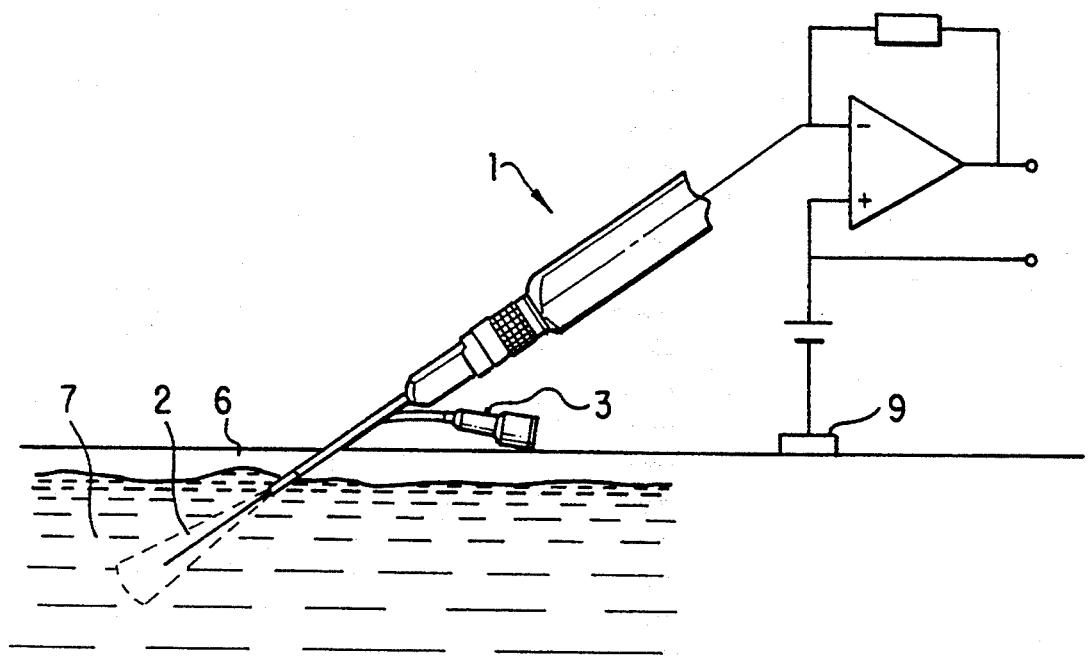
FIG. 1 illustrates the measuring principle with the aid of a representation of the measuring probe.

FIG. 1 illustrates the measuring principle for the measurements of the oxygen partial pressure. The measurements were always performed one hour before and after the stockings or the vest were worn. The oxygen pressure was determined by means of a histograph 1. The skin 6 was pierced by a cannulla 3. A 0.35 mm thin gold measuring probe 2 was inserted into this cannulla 3. This probe 2 was biased against an Ag/AgCl counter electrode 9 with approximately 700 mV. The current flowing in response thereto has a strength which is proportional to the oxygen partial pressure in the connecting electrolytes, in this case consequently the muscle tissue of the test person. By means of an automatic, programmed system the probe 2 is pushed step-by-step into the musculature 7. Each respective measuring period is so short that disturbances of the oxygen partial pressure in the musculature 7 caused by the mechanical pressure of the probe 2 itself on the environment are not to be expected. Performed were 200 measurements which were effected in a predetermined muscle area. This ensures that the calculated mean value represents the actual situation. Before the oxygen partial pressure measurement, the cloth temperature was always recorded by means of a fast-reaction sensor.

Test Performance

Test series 1 has for its object to compare different materials for stockings and measurements in the thigh musculature to each other.

The test persons were 16 healthy persons, men and women in the age group from 20 to 31. They were requested to avoid physical exertion in a period of three hours before the measurement and to rest thoroughly before the start of the test. The measurements were made in a lying position. The skin was not anesthesized.

After the guiding cannulla 3 had been inserted through the skin 6, the temperature in the tissue was first measured and thereafter the oxygen partial pressure measuring probe 2 was inserted. The overall measuring period was 4 minutes. Then the guiding cannulla 3 was removed and the stocking—produced from the different fibers—was drawn over the leg. It then reached from the ankle to the groin. The stocking was kept on for one hour. The test person was requested to put as little strain on his leg musculature as possible.

Test series 2 had for its object to show the effect as regards the increase in the oxygen partial pressure, during wearing of vest-like undershirts of PVC-A-fibers.

The tests were performed on eight persons. The measurements were made in accordance with the same schedule as in test series 1. The vest was also worn for one hour. In order to keep the very disturbing breathing motions in the spinal region as small as possible, much value was attached to a comfortable prone position.

Results

Figure 2:
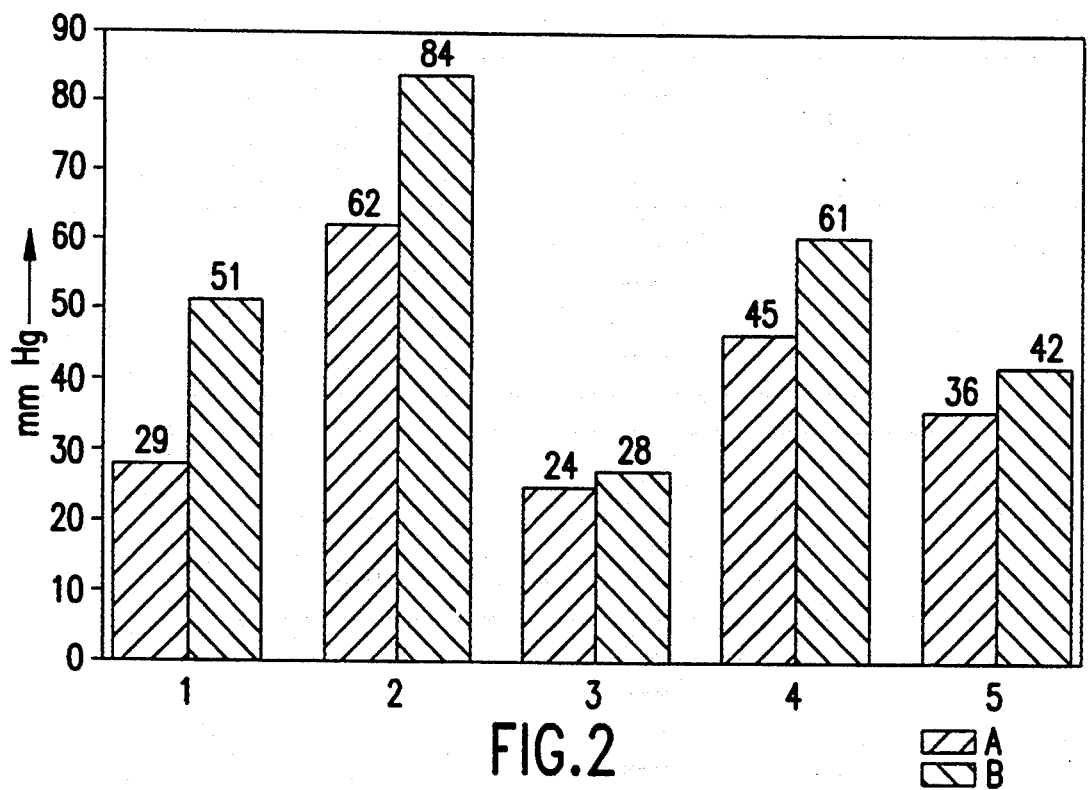
FIGS. 2 to 8 show the individual results for a first test series and FIGS. 9 to 12 show the individual results for a second test series.
Figure 3:
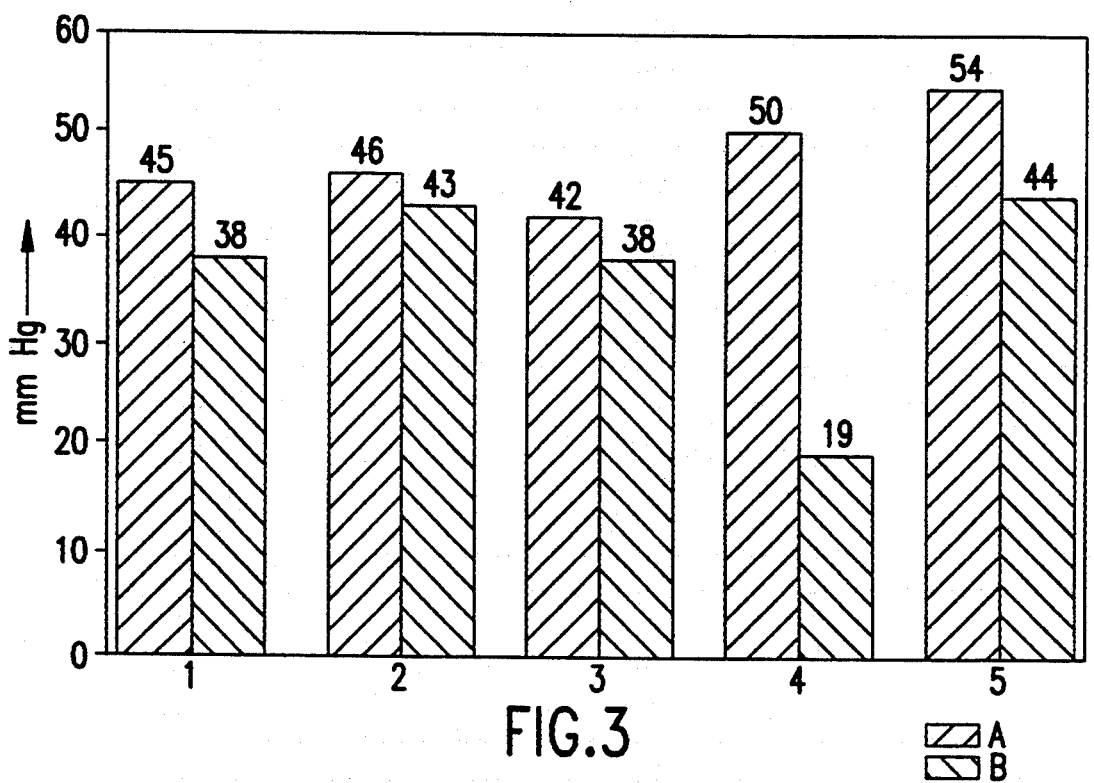

Test series 1: FIGS. 2 to 8 show the measuring results. FIG. 2 shows the tissue oxygen partial pressure in mm Hg for test persons of the group I (PVC-A-fiber stockings), wherein A is the starting value and B is the value after the stockings had been worn for one hour. FIG. 3 shows these values for the group II (cotton stockings).

Figure 4:
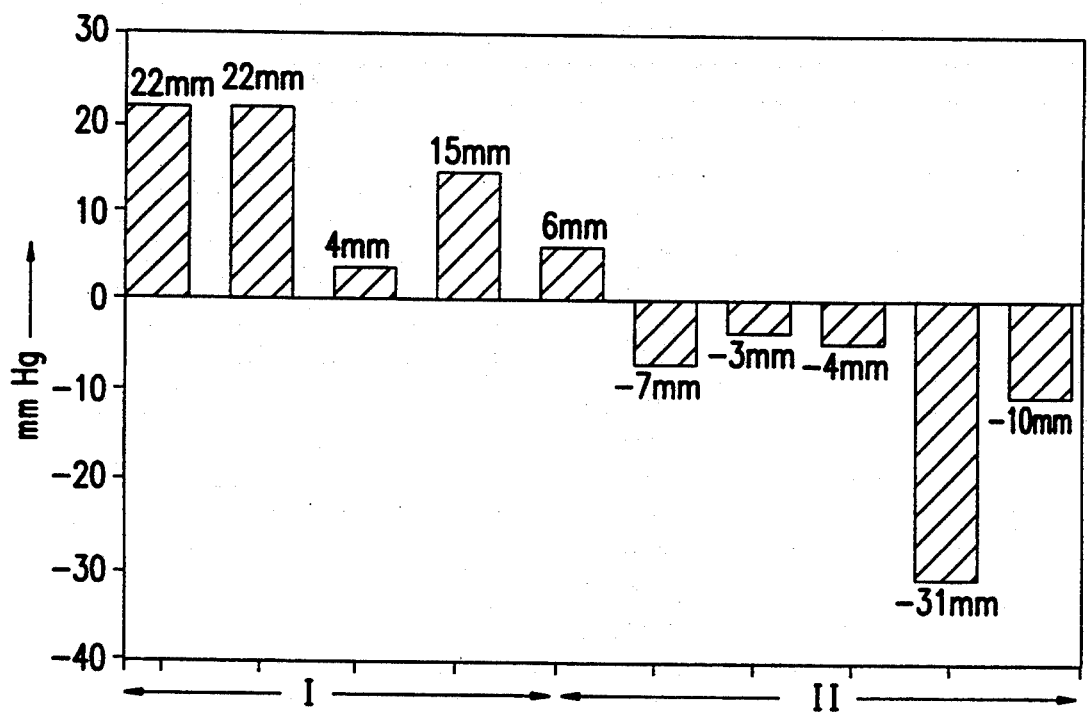
Figure 5:
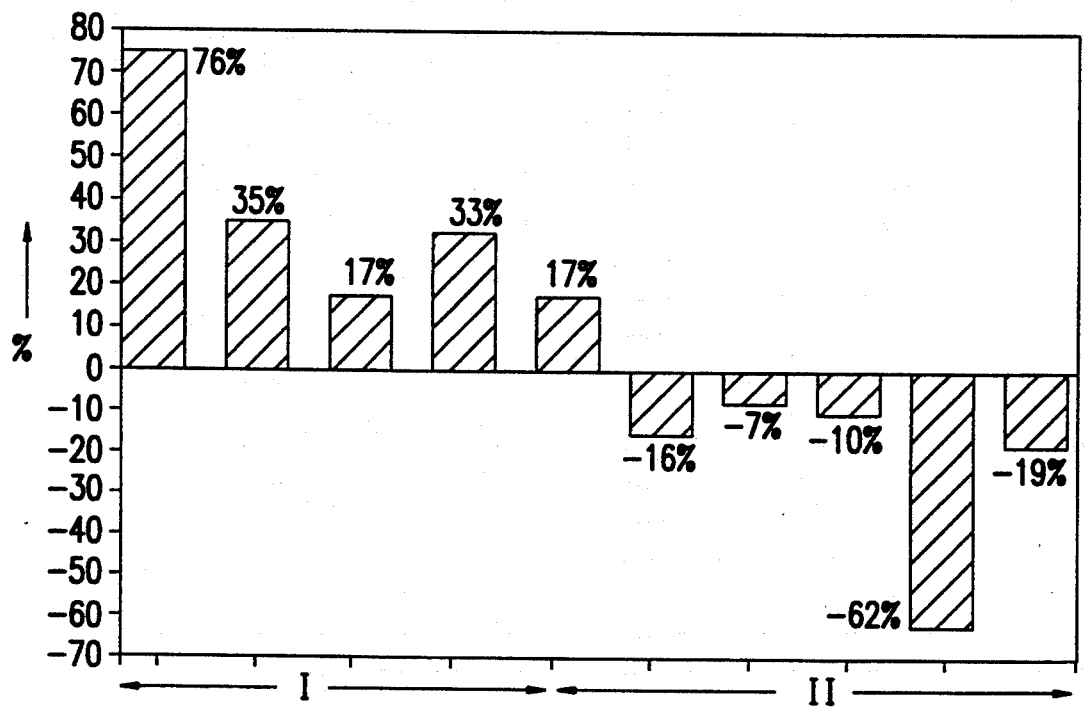

FIGS. 4 and 5 show the increase and the decrease, respectively, of the oxygen partial pressure for both groups: FIG. 4 in mm Hg, FIG. 5 in a percentage figure.

For each test person of group I, the oxygen partial pressure increase after the PVC-A-stocking had been worn for one hour. For each test person of group II, the oxygen partial pressure decreases after the cotton stocking had been worn for one hour. The extent to which the oxygen partial pressure decreases during wearing of the cotton stockings is determined, not insignificantly by the type and quantity of admixtures. Thus, the decrease in the oxygen partial pressure for stockings made of pure cotton shows the highest value: if, for example, elastic acrylic crimped threads were added, then the decrease—as could be expected from the tests—is less.

Figure 6:
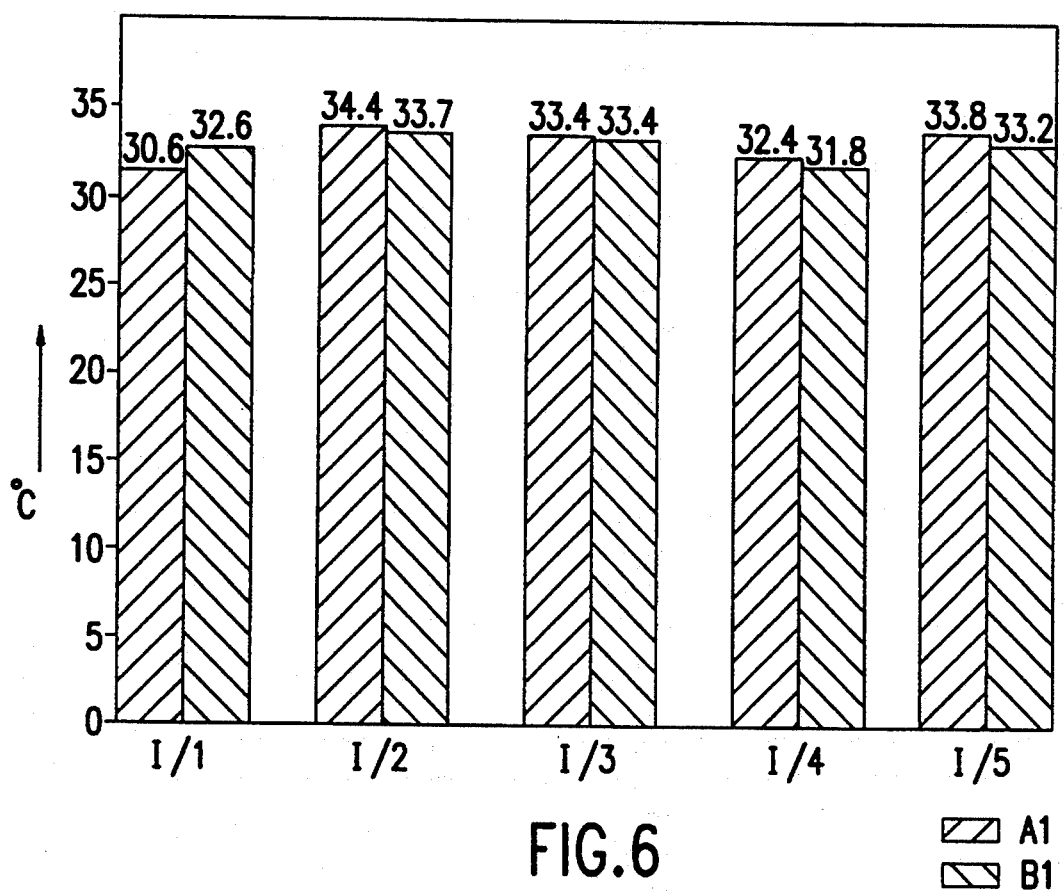
Figure 7:
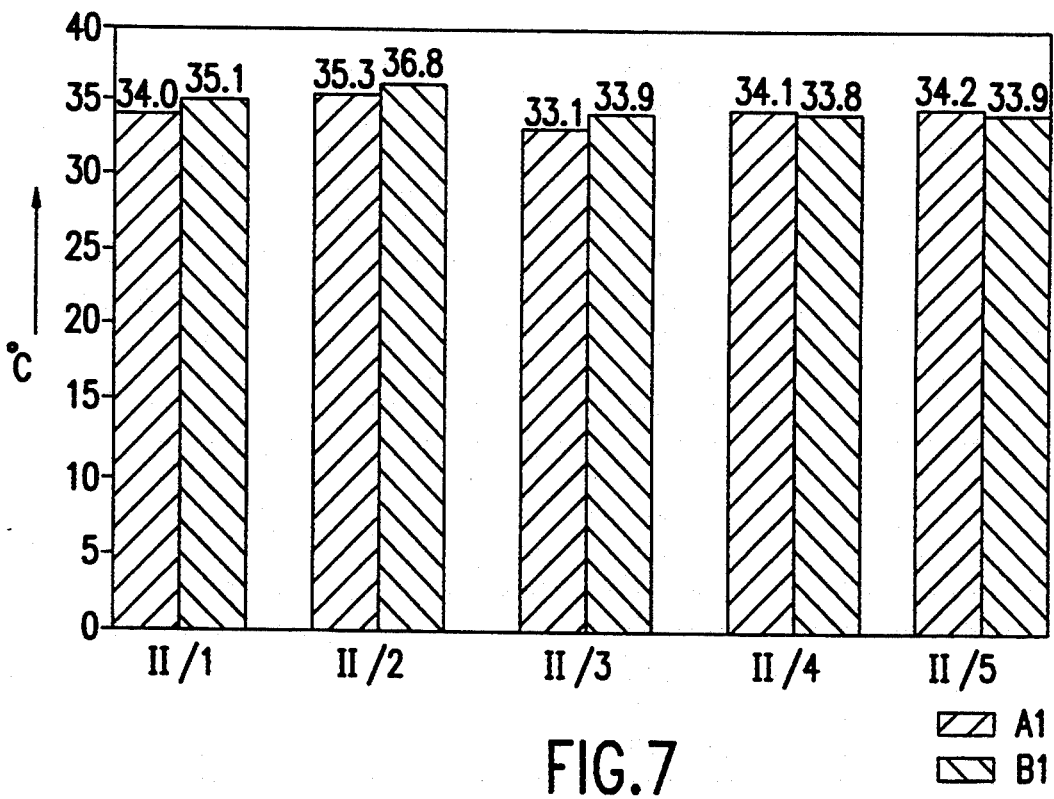

FIGS. 6 and 7 show the starting values A1 and the values B1 (after the stockings had been worn for one hour) of the tissue temperature of the test persons, wherein FIG. 6 shows the results for test persons wearing the PVC-A-fiber stockings and FIG. 7 shows the results for the test persons wearing the cotton stockings. The changes in temperatures were so low that they can be ignored. Although also the starting values A1 of the two groups differ in spite of the randomisation, they are still within the standard range, although for group I more in the lower and for group II in the upper standard range. For the test persons of group I the mean value of the change in the tissue temperature was located at −0.02° C., for the test persons of the group II at −0.56° C.

Figure 8:
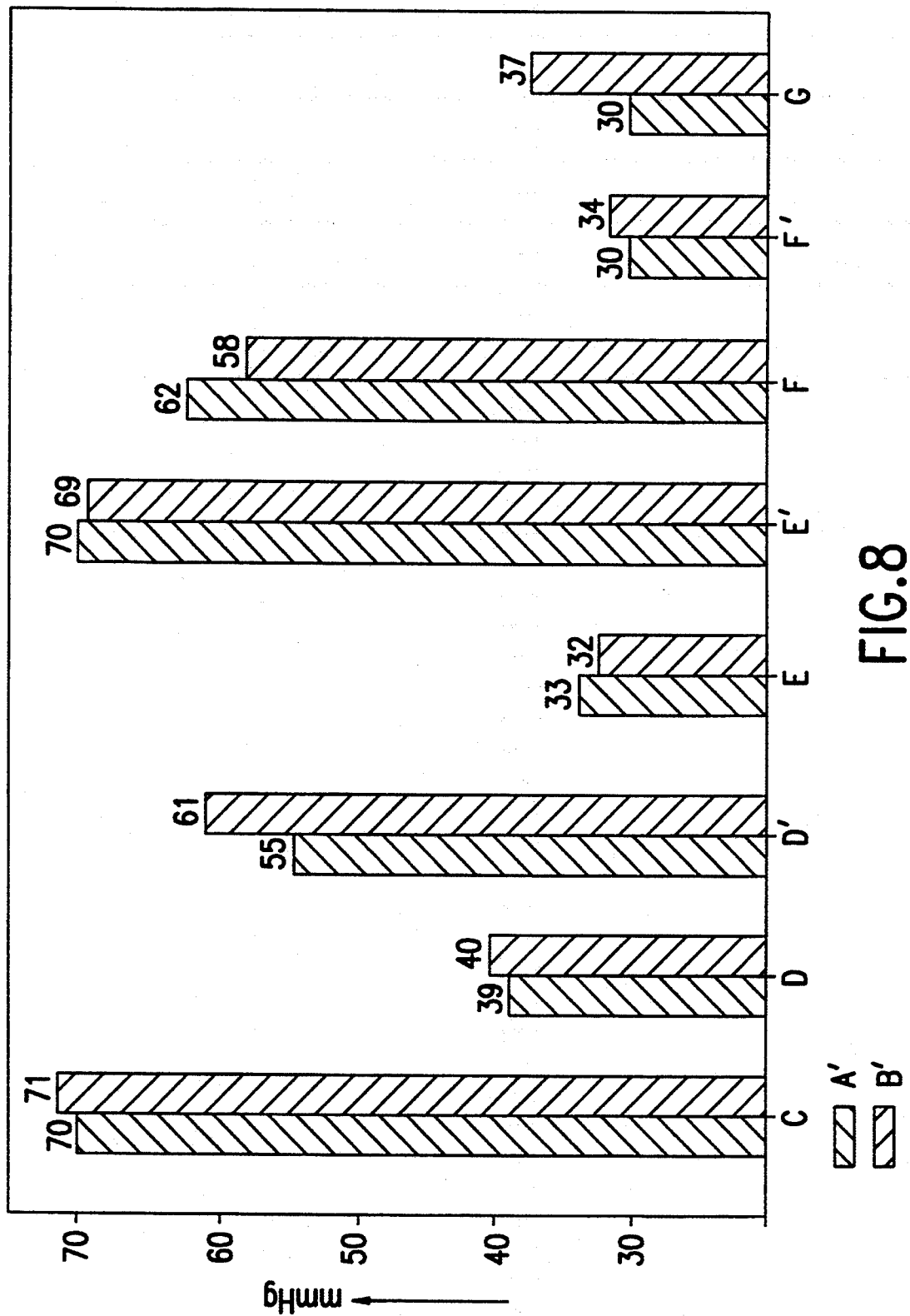

FIG. 8 shows the average change in the oxygen partial pressure in a percentage figure for test persons wearing stockings of 100% acryl (C), 100% polyamide (D), 100% wool (E), 100% silk (F) and 100% PVC (G). Also in this case the respective starting values A' and the values B' (after wearing of the stockings for one hour) of the test persons are plotted against each other.

Test Series 2

FIGS. 9 to 12 show the results of this test series. The increase in the oxygen partial pressure has a different value for the individual persons. Test persons for which the prone position caused no difficulties, and who during the measurements could refrain from abdominal respiration, showed in each case an increase in the oxygen partial pressure or at least constant values. It should however be born in mind, that motions of the musculature which cause a change in posture, may significantly disturb the measuring results. Although this did not cause problems during performing of the test series 1, problems arose in the test series 2, as part of the test persons in the prone position had complaints.

Figure 9:
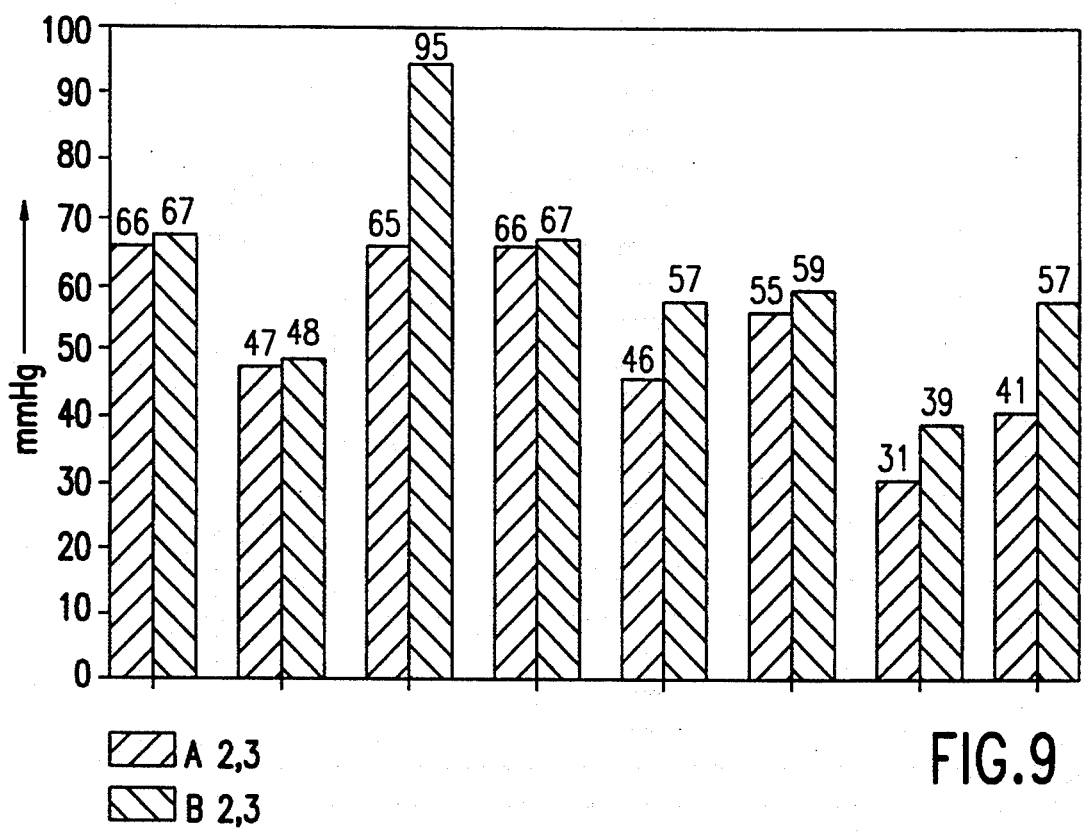

FIG. 9 shows the starting values A2 and the values B2 for the oxygen partial pressure after one hour's wearing of the vest.

Figure 10:
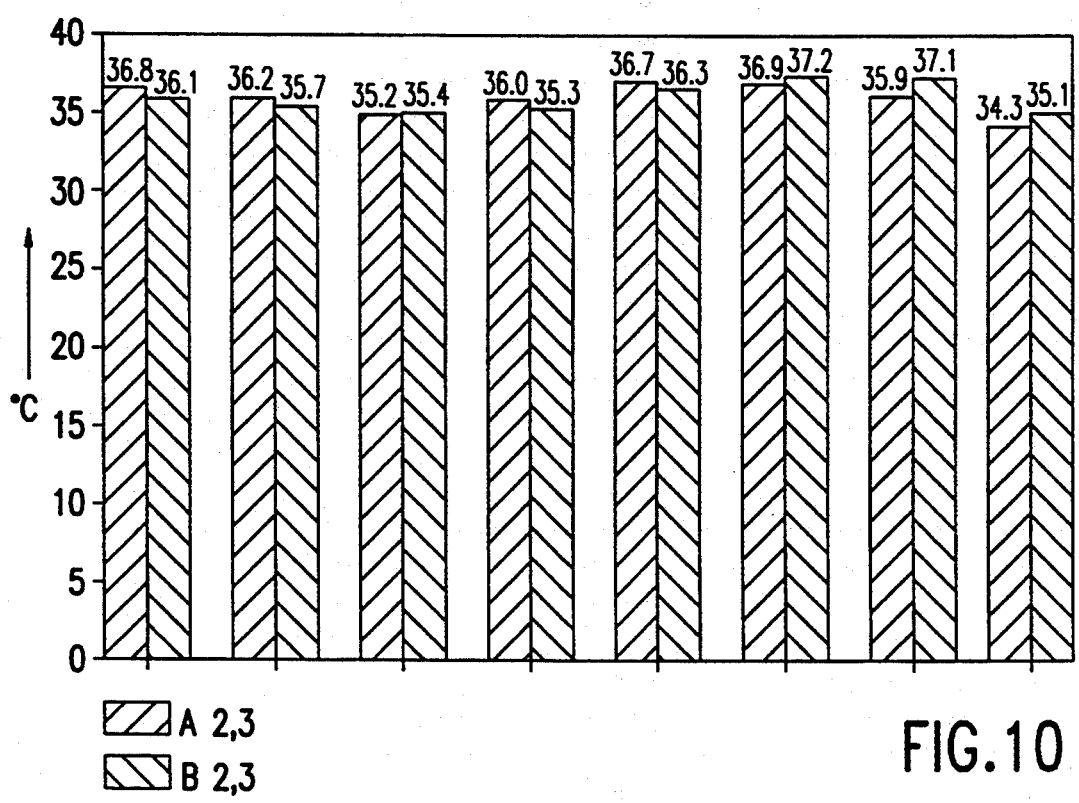

FIG. 10 shows the corresponding values A3 and B3 of the tissue temperature.

Figure 11:
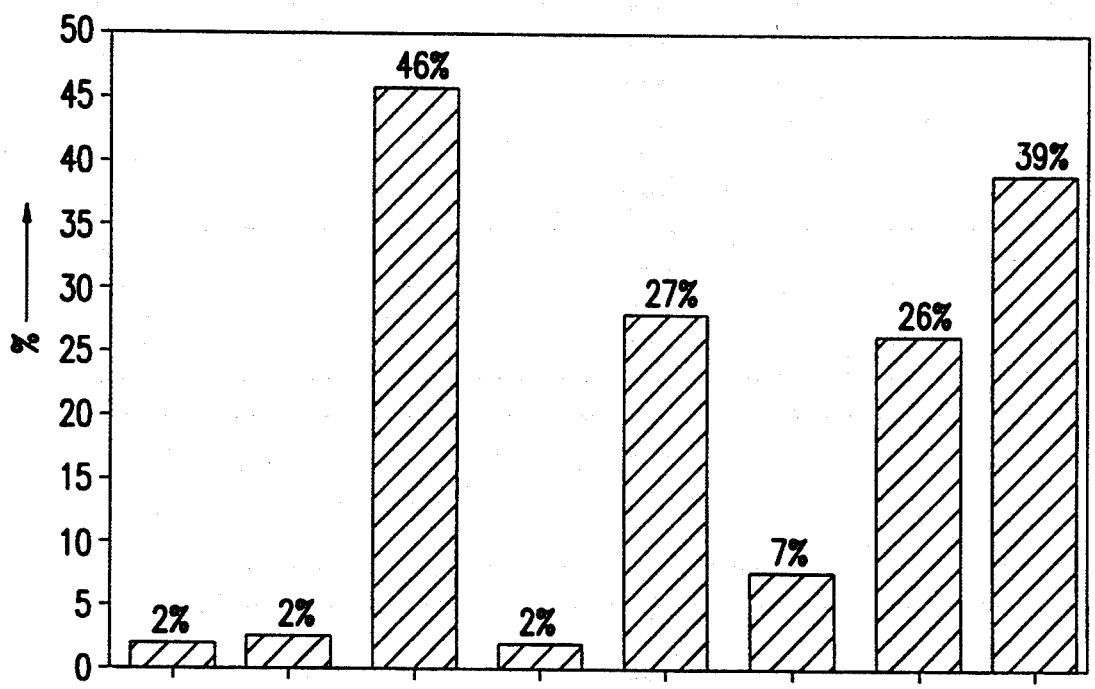
Figure 12:
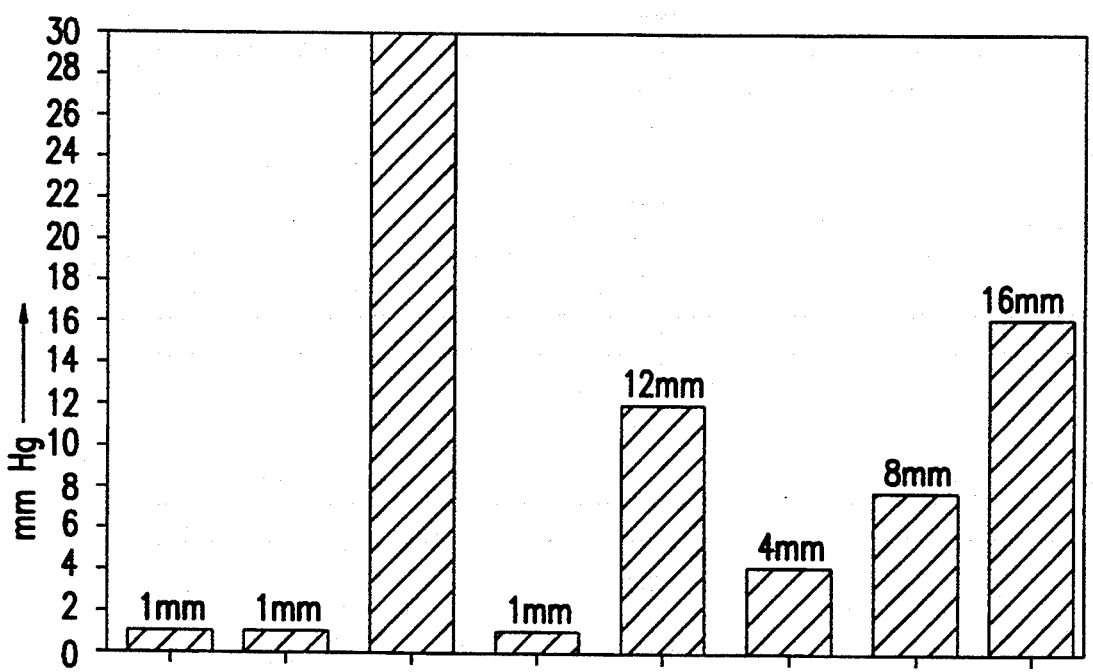

FIGS. 11 and 12 show the increase in the oxygen partial pressure, FIG. 11 showing the increase in mm Hg and FIG. 12 in %.

Discussion

The results of the two test series: measuring problems: the measurement of the oxygen partial pressure by means of an inserted probe is, as mentioned in the foregoing, beset with methodical difficulties. Inserting a measuring catheter inevitably causes irritations in the measuring region of the tissue, and it may cause a distinct influence on the blood circulation and consequently on the supply of oxygen. So as to maintain these problems, a very fine probe having a diameter of 0.35 mm was used. It was reciprocated at predetermined intervals of the tissue, and adjusted to new measuring positions by rotating the needle holder. Since the measuring period was extremely short, disturbances in the oxygen partial pressure due to the compressive pressure, if any, could not occur until after the measuring procedure. Measuring errors if any, may however be attributable to the type of tissue. The musculature with its plurality of structures can definitely also produce extraordinary measuring results, depending on in which part of the tissue measurements are predominantly made. By selecting the measuring region carefully it was nevertheless tried to ensure that the average of 200 measuring data represents the actual oxygen partial pressure. However, a condition therefore was a musculature in rest, as the measuring system was rigidly attached and scanned the predetermined measuring region.

Starting values A: the starting value A for the oxygen partial pressure was located in the range expected on the basis of other measurements. In dependence on the training-dependent myoglobin content the highest values were found in sportsmen participating in sports which requiring a lot of stamina. Similar to the tissue temperature the oxygen partial pressure decreases versus the distance between the musculature and the body center. The further the musculature is removed from the center of the body the lower are the tissue temperature and the oxygen partial pressure in rest. For a better comparison of the results, it was tried to keep the spread in the starting values as small as possible. The test persons were accordingly requested not to do any physical work four hours before the measurement and in particular not to participate in any sport. Extreme values, as shown by test person 2 of group I (FIG. 2) may be based on the fact that in that case a very highly trained sportsman is involved.

Test series 1: For all the test persons of group I, who wore stockings made of PVC-A-fibers, an increase was found, after one hour's wear, of the oxygen partial pressure in the thigh muscle. For all the test persons of group II, who wore cotton stockings, a decrease in the oxygen partial pressure was found. A significant increase in the oxygen partial pressure could also be found for test persons who had worn stockings of pure polyvinyl chloride or polyamide, respectively.

Test series 2: As was to be expected, here the starting value for the tissue temperature was near the temperature in center of the body. No comparative measurements were made for the measured starting values of the oxygen partial pressure. Although in the case of an incorrect position of the spinal column, of which some test persons suffered, higher oxygen partial pressure values due to a heavier demand on the spine musculature are quite possible, these values decrease in a more restful position. An increase in the oxygen partial pressure in the lumbar musculature was in general also measured for those test series in which the test persons wore vests of PVC-A-fibers.

Figure 13:
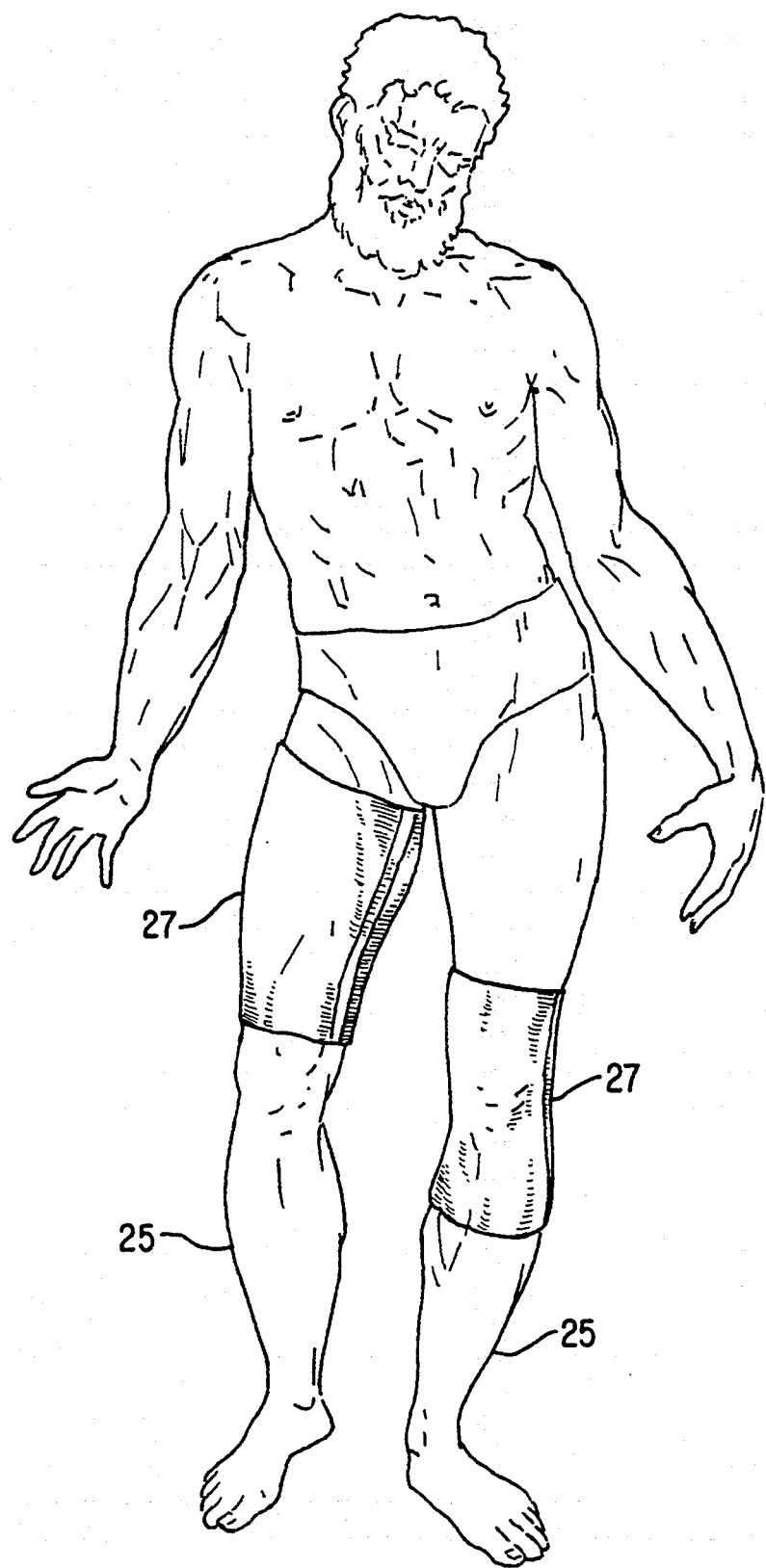
FIGS. 13 to 15 illustrate the application of the cloth in the form of stockings, bandages and undergarments to the musculature of a human.
Figure 14:
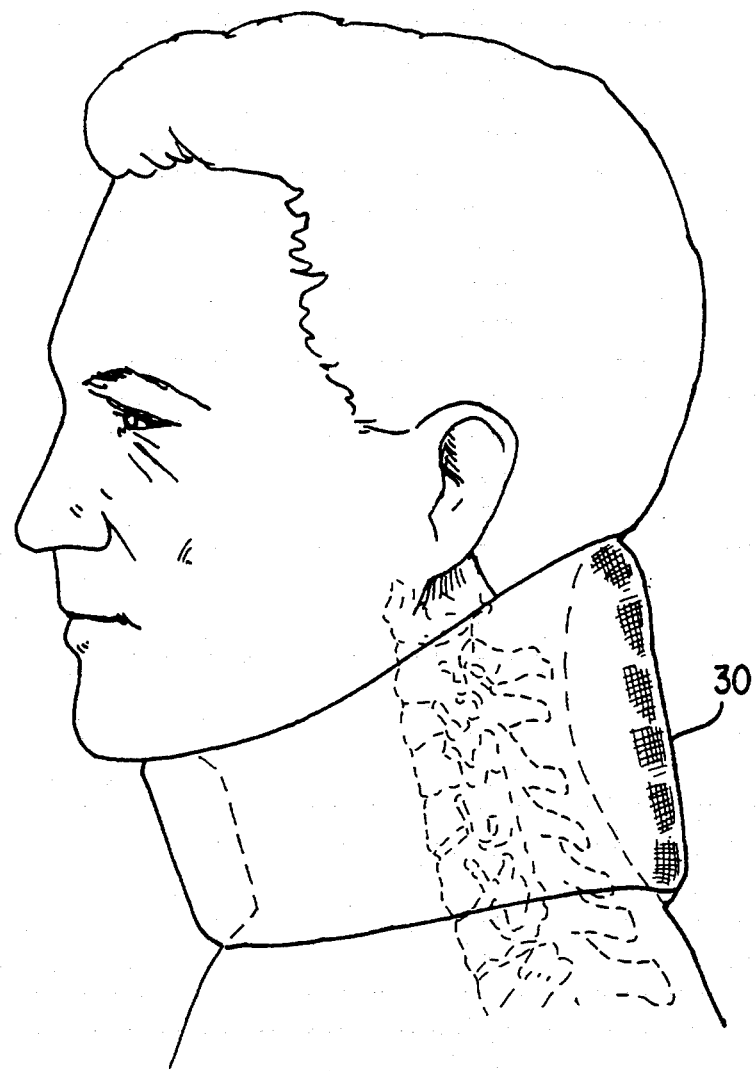
Figure 15:
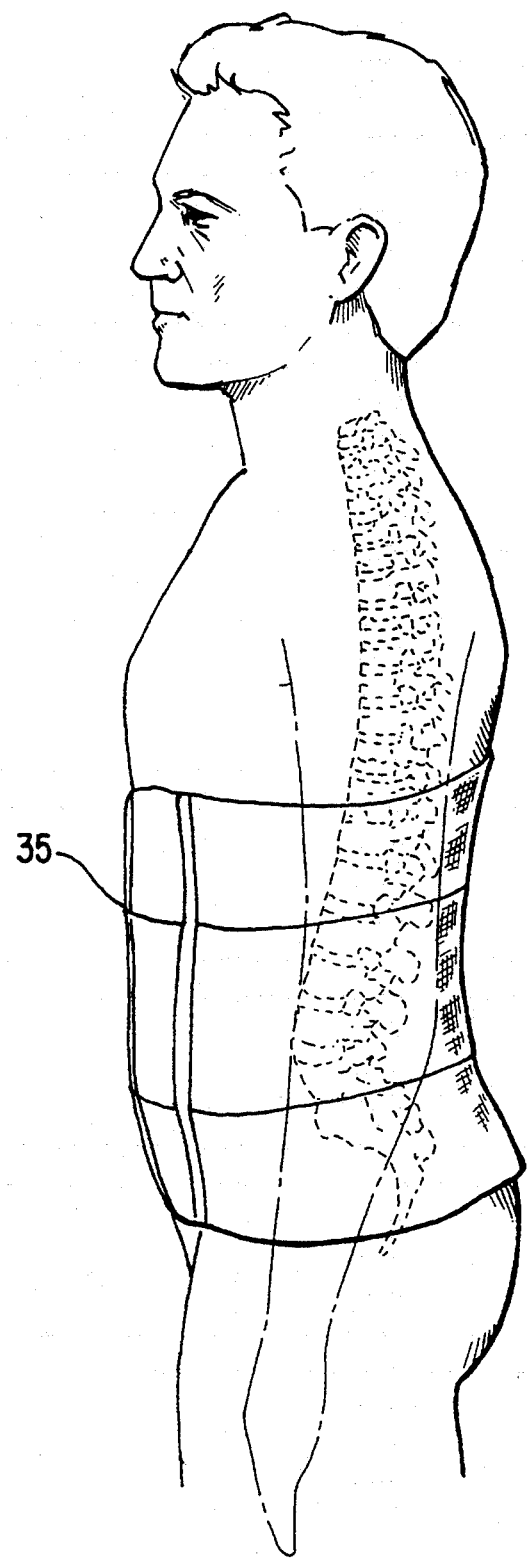

FIGS. 13 to 17 are illustrative examples of the application of the woven cloth to the musculature of humans and animals. In FIG. 13, the cloth is shown as applied to the leg limbs 25 of a human in the form of a bandage or stocking 27. In FIG. 14, the cloth 30 is shown as applied to the musculature of a human neck. In FIG. 15, the cloth is shown in the form of an undergarment 35 around the midsection of a human.

Figure 16:
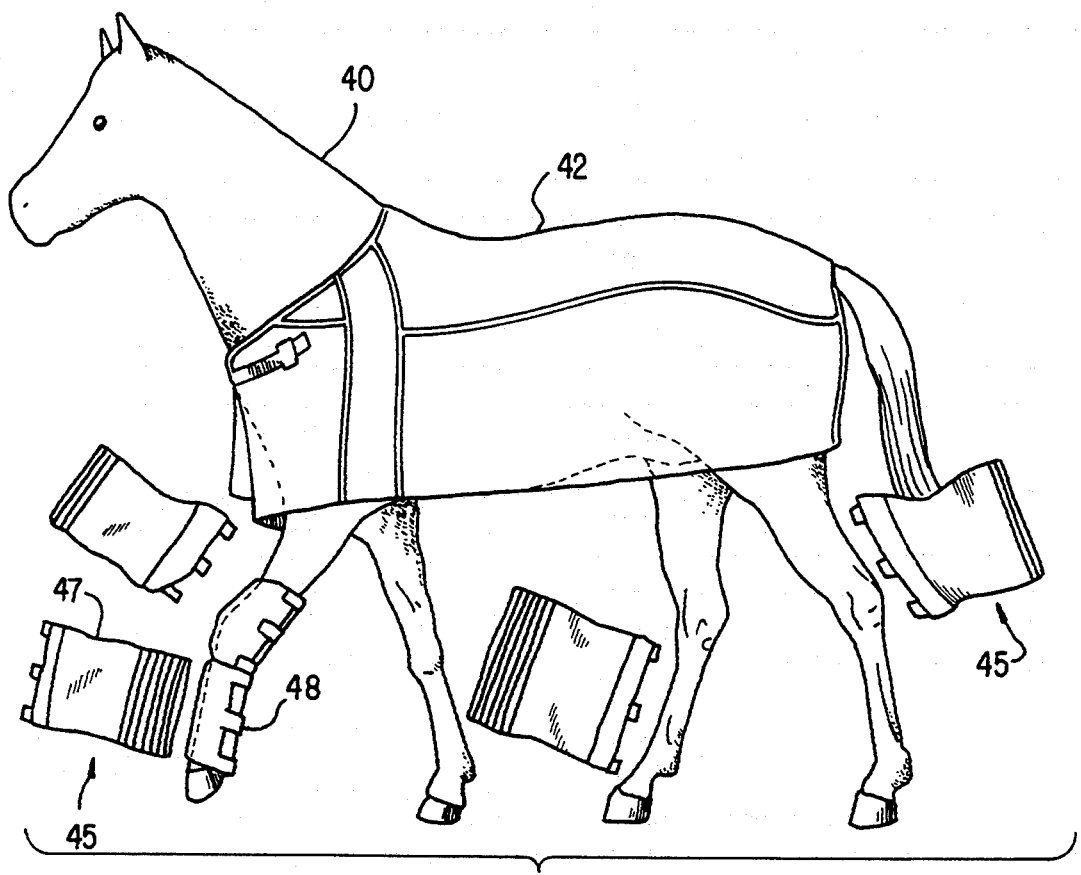
FIG. 16 illustrate the application of the cloth in the form of bandages and horse-cloth to the musculature of a horse.

FIG. 16 illustrates some example applications of the cloth of the present invention to the musculature of a horse 40. The cloth may be applied as a horse-cloth 42 or as a bandage 45. On the front leg of the horse in FIG. 16, the bandage 45 is shown in position 47 prior to application and position 48 following application.

Figure 17:
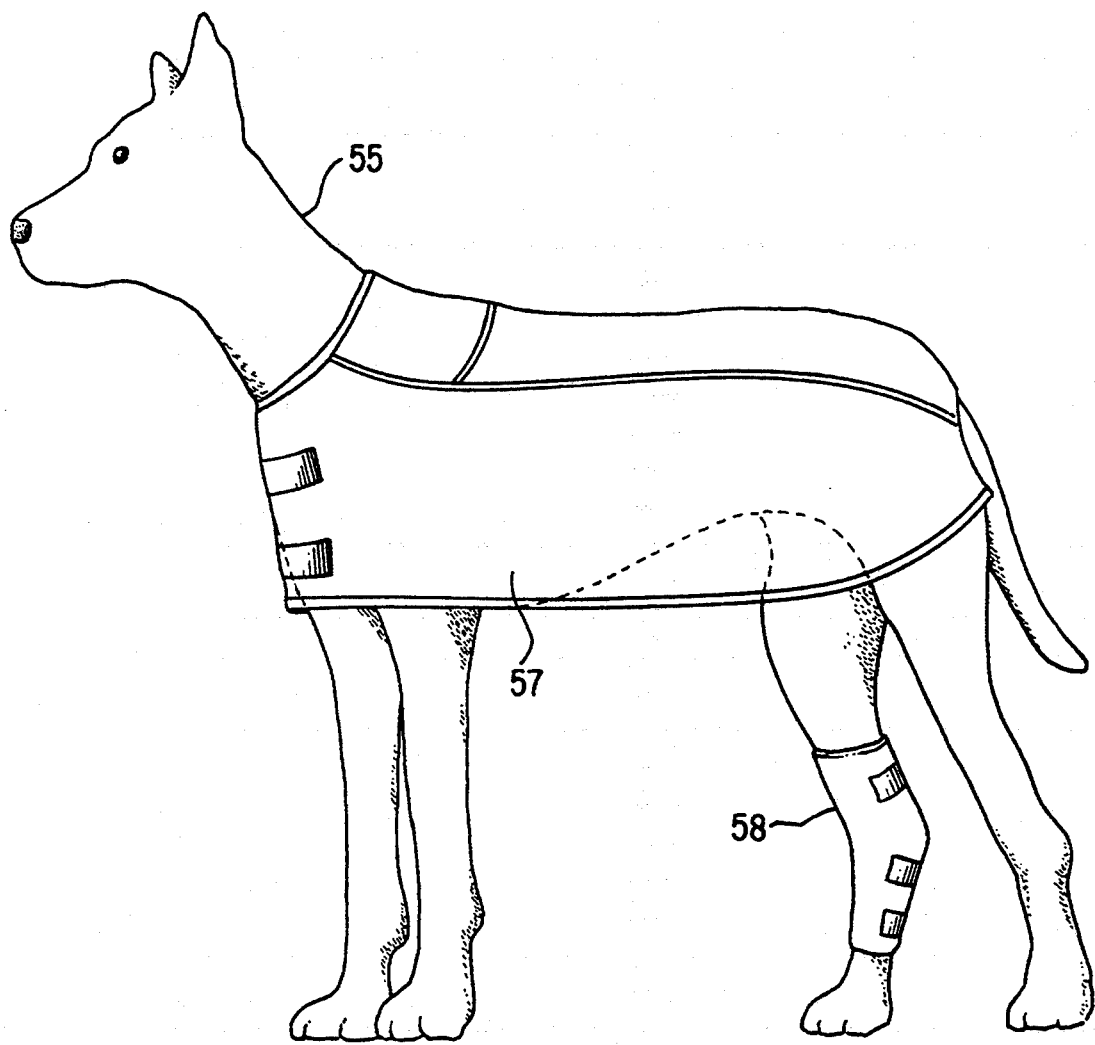
FIG. 17 illustrates the application of the cloth in the form of a bandage and cover-cloth to the musculature of a dog.

FIG. 17 illustrates examples of the application of the cloth of the present invention to the musculature of a dog 55. The cloth is shown in the form of a cover-cloth 57 and as a bandage 58.

I claim:

1. A method of increasing the oxygen partial pressure in musculature of an animal or a human comprising:
applying to said musculature a woven cloth comprised of at least 50% by weight of at least one of polyvinyl chloride fibers and polyamide fibers, said cloth including less than 10% by weight of at least one of cotton fibers and rayon fibers.

2. The method of claim 1, wherein said cloth is comprised of at least 50% by weight of polyvinyl chloride fibers and no more than 25% by weight of acrylic fibers.

3. The method of claim 2, wherein said cloth is comprised of more than 75% by weight of said polyvinyl chloride fibers.

4. The method of claim 1, wherein said cloth also includes wool fibers.

5. The method of claim 4, wherein said wool fibers include angora fibers.

6. The method of claim 1, wherein said woven cloth is applied to the musculature of a human in the form of an undergarment.

7. The method of claim 6, wherein said woven cloth undergarment is applied to the musculature of the human during the performance of warming-up activities by said human.

8. The method of claim 1, wherein said woven cloth is applied in the form of a bandage to a limb of the animal or human to treat disturbances in the arterial blood flow of said limb.

9. The method of claim 1, wherein said woven cloth is applied in the form of a stocking to a limb of the animal or human to treat disturbances in the arterial blood flow of said limb.

10. The method of claim 1, wherein said woven cloth is applied to the musculature of a horse.

11. The method of claim 10, wherein said woven cloth is applied as a bandage to the horse during the performance of warming-up activities by the horse.

12. The method of claim 10, wherein said woven cloth is applied in the form of a horse-cloth during the performance of warming-up activities by the horse.

13. The method of claim 1, wherein said woven cloth is applied to the musculature of a dog.

14. The method of claim 13, wherein said woven cloth is applied in the form of a bandage to said dog.

15. The method of claim 13, wherein said woven cloth is applied in the form of a cover-cloth to said dog.

16. The method of claim 1, wherein said cloth also includes silk fibers.

* * * * *